United States Patent [19]

Borgen

[11] 4,135,495

[45] Jan. 23, 1979

[54] METHOD AND MEANS FOR REVERSIBLE STERILIZATION

[76] Inventor: Jennings O. Borgen, 1100 University, Apt. 3J, Seattle, Wash. 98101

[21] Appl. No.: 579,484

[22] Filed: May 21, 1975

[51] Int. Cl.² ........................................... A61B 19/00
[52] U.S. Cl. ........................ 128/1 R; 128/DIG. 25; 3/1
[58] Field of Search ............... 128/1 R, DIG. 25; 3/1

[56] References Cited

U.S. PATENT DOCUMENTS

| | | | |
|---|---|---|---|
| 3,422,813 | 1/1969 | Helmer | 128/1 R |
| 3,562,352 | 2/1971 | Nyilas | 128/1 R |
| 3,646,616 | 3/1972 | Keshin | 3/1 |
| 3,646,929 | 3/1972 | Bonnar | 128/1 R |

FOREIGN PATENT DOCUMENTS 1161436  8/1969  United Kingdom ............................ 3/1

OTHER PUBLICATIONS

Stanley et al., Bladder Regeneration, Trans. Amer. Soc. Artif. Int. Organs, 1971, pp. 134–138.

*Primary Examiner*—Jerome Schnall
*Attorney, Agent, or Firm*—Seed, Berry, Vernon & Baynham

[57] ABSTRACT

Method and means for reversible sterilization of females in which caps are placed over the fimbriated ends of the Fallopian tubes and sutured to the serosa thereof. The caps block passage of sperm and ova to prevent pregnancy. The caps can be sutured to and removed from the ends of the Fallopian tubes without damage to the transport mechanism of the tubes.

5 Claims, 5 Drawing Figures

U.S. Patent  Jan. 23, 1979  4,135,495
FIG. 1
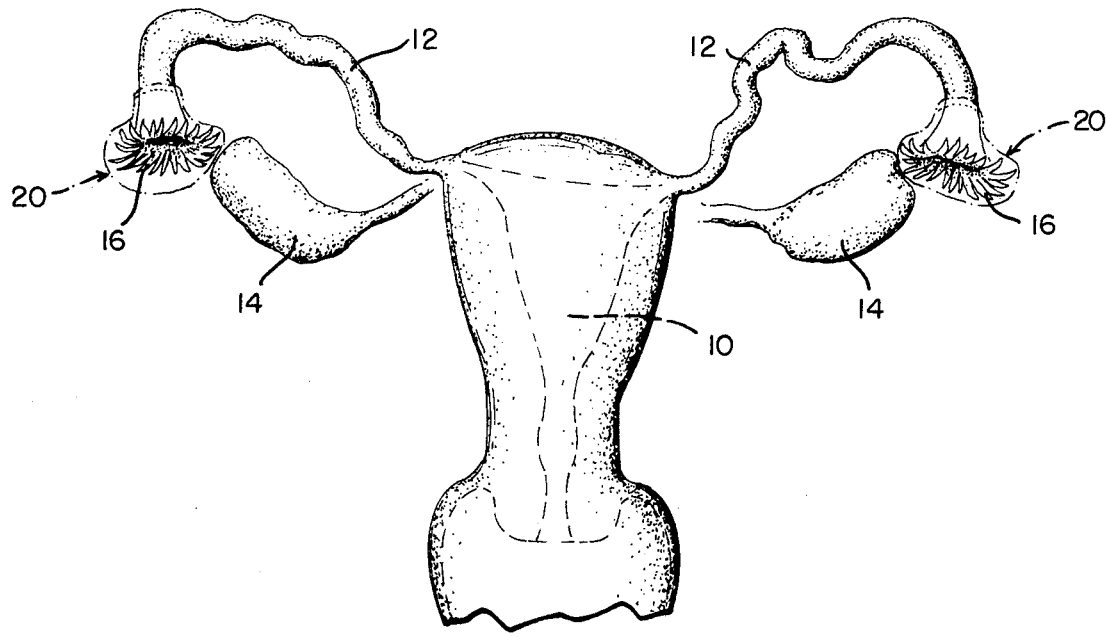
FIG. 2
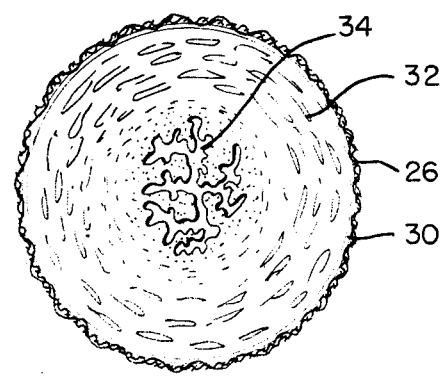
FIG. 5
FIG. 3
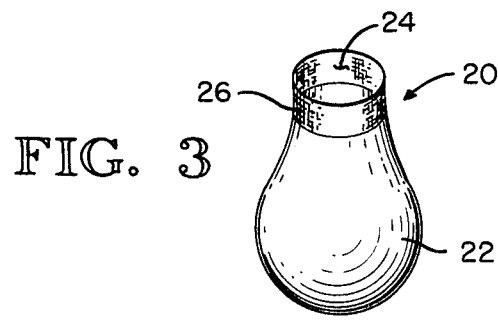
FIG. 4
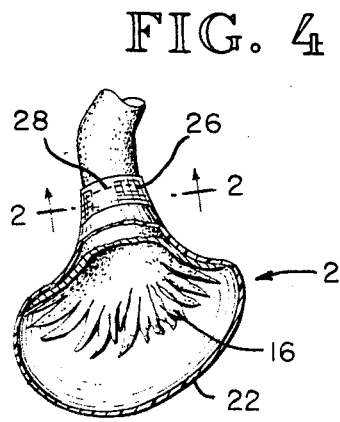

METHOD AND MEANS FOR REVERSIBLE STERILIZATION

BACKGROUND OF INVENTION

The invention relates to a method and apparatus for a surgical, reversible sterilization of females.

As is generally recognized, birth control has been relied upon as the principal means to control over-population in the world. In the field of birth control the prevention of conception is considerably more acceptable for controlling population growth than for females to submit themselves to abortion. However, the methods heretofore proposed for contraception have had inherent drawbacks which limit their applicability and effectiveness. Ideally, contraception should be 100% effective in preventing conception; it should not rely on will power and should not interfere with the sexual relationship; and it should be simple and low in cost. It should not have harmful, psychological side-effects. A very important feature of an ideal contraceptive method is that it be reversible so that it can be resorted to for family planning so that addition children may be had if desired.

Numerous techniques of contraception have been employed. Birth control pills for instance, have disadvantages and are controversial. Mechanical devices such as condoms, diaphragms and vaginal foams are awkward and unreliable. Additionally, surgical methods have included rings, clamps and plugs of various types. Also interuterine devices have fallen out of favor because of other disadvantages. Surgical techniques so far employed have had a common failing. They interfere with, block, or damage the transport mechanism of the Fallopian tubes. Stated another way, injury is caused to the celliated cells and/or to the muscular layer of the tube, or the surgical technique may effect complete separation of a portion of the tube. In addition, other techniques have been too complicated for the average operator in that they require sophisticated equipment either to install or attach a device, or to cut or coagulate the tube. These methods are not really reversible because of the injury they cause to the transport mechanism. It is not maintained that all of the techniques which purport to be reversible are not in fact so, but, injuries to those parts of the Fallopian tubes above identified are not usually reparable and therefore reduce the patient's chances of become pregnant again.

SUMMARY OF THE INVENTION

In accordance with this invention a method and apparatus are provided to obstruct the Fallopian tubes of the human female in a manner which does not injure the tube's internal transport capability. A cap device is placed over the fimbriated end of the Fallopian tube and sutured to the serosa. The cap material is an inert, soft thin walled, flexible, light, medical grade elastomeric material which may also be radio opaque. Suturing of the cap is confined to the serosa of the tube. The material is such that it will not cause tissue reaction or adhesions.

Accordingly, it is among the features and advantages of this invention to provide a method and apparatus for the reversible sterilization of females which is a relatively simple and inexpensive operative procedure. The invention satisfies a great need as well as being highly desirable by many. The procedure involves some post-operative discomfort to the patient that always associates with an incision in the stomach but is certainly less than the discomfort associated with a Caesarean section. The operation is not as major as an appendectomy. The procedure can be performed by most doctors who do surgery. The procedure provides a reliable method of reversible sterilization. The method and apparatus of this invention offer an opportunity for a woman to change her mind about child bearing. It enables a woman, who may decide that she does not want to get pregnant, to avoid subjecting herself to permanent sterilization. The invention may be more acceptable to women who for one reason or another are disinclined to the use of pills, IUD's or other birth control methods and devices. The procedure does not interfere with perastolsis of the tube which is part of the tube transport capability. The cap can be surgically removed, restoring full, normal conception capability.

BRIEF DESCRIPTION OF DRAWING

FIG. 1 is an illustration partly in cross-section showing uterus, Fallopian tubes and ovaries and location of caps;

FIG. 2 is a typical cross-sectional view through a Fallopian tube to illustrate general details of its structure and to illustrate suturing of the cap to the outer layer or serosa of the tube;

FIG. 3 is a perspective view illustrating additional details of the cap;

FIG. 4 is a further illustration, partially in cross-section showing a cap sutured into place over the fimbriated end of a Fallopian tube; and FIG. 5 is an enlarged portion through a Fallopian tube illustrating suturing of the cap to the outer layer or serosa of the tube.

DESCRIPTION OF PREFERRED EMBODIMENT

The FIG. 1 represents the organs concerned including uterus 10, Fallopian tubes 12, ovaries 14 and the fimbriated Fallopian tube ends 16. The abdomen of the patient is opened with a small lower abdominal incision. Each individual tube is then brought up in turn to the incision. The caps, generally identified by the number 20, are made up of a solid portion 22 in the form of a round flat or oblong sack-like article which is generally large enough to surround and encase the tube fimbria while at the same time enabling some freedom of movement for the fimbria. The tube itself on an average is about ½ centimeter in diameter proximal to the fimbria. The solid cap portion 22 will be in the area of 2 to 2½ centimeters across and it will have an open end 24 approximately the size of the tube. It will be understood that the term "solid" as used herein embraces not only a continuous or solid thin wall but any satisfactory material which is impervious to the passage of sperm or ova. The cap opening 24 may be defined by a slightly tapering extension of portion 22 so that a piece can be cut off to match the suturing section size to the Fallopian tube. More preferably, however, the cap section 22 will have bonded or sealingly attached thereto a suturing section 26 of fine mesh also of an inert medical grade elastomeric material. It is not essential that cap portion 22 and suturing strip 26 be of the same material. Suturing portion 26 on the open end 24 of cap section 22 is to facilitate suturing. The solid cap portion 22 is an inert medical grade silicon elastomeric material such as silicon rubber, but which is also thin walled, flexible and preferable radio opaque. The material from which the cap is made, including the suturing strip 26, is the type of base material which would not cause tissue reaction or adhesions. It is contemplated that other medical grade plastic materials such as Dacron or Teflon can be used for both the cap and suturing strip.

As can be seen in FIGS. 2 and 5 after the individual tubes are brought up to the incision the caps are placed over the end of the fimbriated tube and secured to the serosa by sutures 28. The tube has outer layer or serosa 30, muscular layer 32 and tube interior which is generally open but lined with ciliated cells 34. Care is taken in placing the cap over the fimbriated end of the tube that the sutures do not enter the muscular layer 32. The ends of both tubes are thus capped and sutured as described. Fiberblastic proliferation will seal off the union or interface between suturing section 26 of the cap and the serosa. In this way, the small diameter sperm will be unable to pass through the cap or the serosa - cap interface.

What is claimed is:

1. A device for removably capping the fimbriated end of the Fallopian tubes of the human female to provide reverse sterilization without interference with perastolsis of the Fallopian tubes comprising:

an integral one-piece cap of light, thin walled flexible medical grade elastomeric material having (1) an enlarged body portion of a size sufficient to surround and enclose the fimbriated end of a Fallopian tube and (2) an opening in the body portion approximately the diameter of the Fallopian tube, an integral suturing section secured around the opening in the cap conforming essentially to the diameter of the Fallopian tube and extending parallel thereto providing a suturing area for suturing the device to the serosa around the outer circumference of the Fallopian tube so that the body portion of the cap encloses the fimbriated end of the Fallopian tube and provides an impervious barrier to the passage of sperm and ova without interfering with the perastolsis action of the inner ciliated cells of the Fallopian tubes.

2. The device of claim 1 wherein the suturing section tapers from a larger diameter where it connects with the body portion of the cap to a smaller diameter away from the cap so that the size of the opening into the cap can be matched to the diameter of the Fallopian tube by cutting of the suturing section a predetermined distance from the point of connection of the suturing section to the body portion of the cap.

3. The device according to claim 1 wherein the body portion has a bulbous configuration tapering down to the opening, the opening having a diameter slightly larger than the diameter of the Fallopian tubes.

4. The device according to claim 1 wherein the suturing section is made of a fine mesh medical grade elastomeric material sealingly bonded to the body portion of the cap around the opening therein.

5. The device according to claim 2 wherein the diameter of the opening and the diameter of the suturing section are such that when suturing of the device is completed to the serosa of the Fallopian tubes a pregnancy-preventing seal is provided between and around the cap and the Fallopian tubes.

* * * * *